United States Patent [19]

Kliger

[11] 4,170,895
[45] Oct. 16, 1979

[54] ONCOTIC PRESSURE MEASUREMENT CELL

[76] Inventor: Gilbert L. Kliger, 1201 Lindley Ave., Philadelphia, Pa. 19141

[21] Appl. No.: 881,705

[22] Filed: Feb. 27, 1978

[51] Int. Cl.$^2$ .......................................... G01N 13/04
[52] U.S. Cl. ................................................. 73/64.3
[58] Field of Search ....................................... 73/64.3

[56] References Cited

U.S. PATENT DOCUMENTS

| | | | |
|---|---|---|---|
| 3,063,288 | 11/1962 | Reiff | 73/64.3 |
| 4,028,931 | 6/1977 | Bisera et al. | 73/64.3 |

FOREIGN PATENT DOCUMENTS

| | | | |
|---|---|---|---|
| 669342 | 12/1938 | Fed. Rep. of Germany | 73/64.3 |
| 1523472 | 3/1968 | France | 73/64.3 |

*Primary Examiner*—S. Clement Swisher
*Assistant Examiner*—Joseph W. Roskos
*Attorney, Agent, or Firm*—Nelson E. Kimmelman; Edward M. Farrell

[57] ABSTRACT

An oncotic pressure measurement cell which comprises a transparent plastic upper sample chamber and a lower metallic reference chamber into which the lower, threaded ends of vertical clamping rods are anchored. The upper chamber has vertical passageways through which the rods are passed. The lower metallic reference chamber is coupled, in use, to an appropriate pressure transducer. An aperture is formed in the top of the reference chamber which communicates with the interior of the reference chamber and is covered with a semi-permeable membraneous disc made of plastic. A nylon washer is placed over the disc to retain it in place thereby producing a semi-permeable barrier between the chambers. After this upper chamber is moved downwardly with the clamping rods passing through the passageways, thumb nuts are screwed onto the upper ends of the rods thereby forcing the upper chamber downwardly and pressing the nylon washer tightly against the semi-permeable disc.

10 Claims, 3 Drawing Figures

U.S. Patent
Oct. 16, 1979
4,170,895
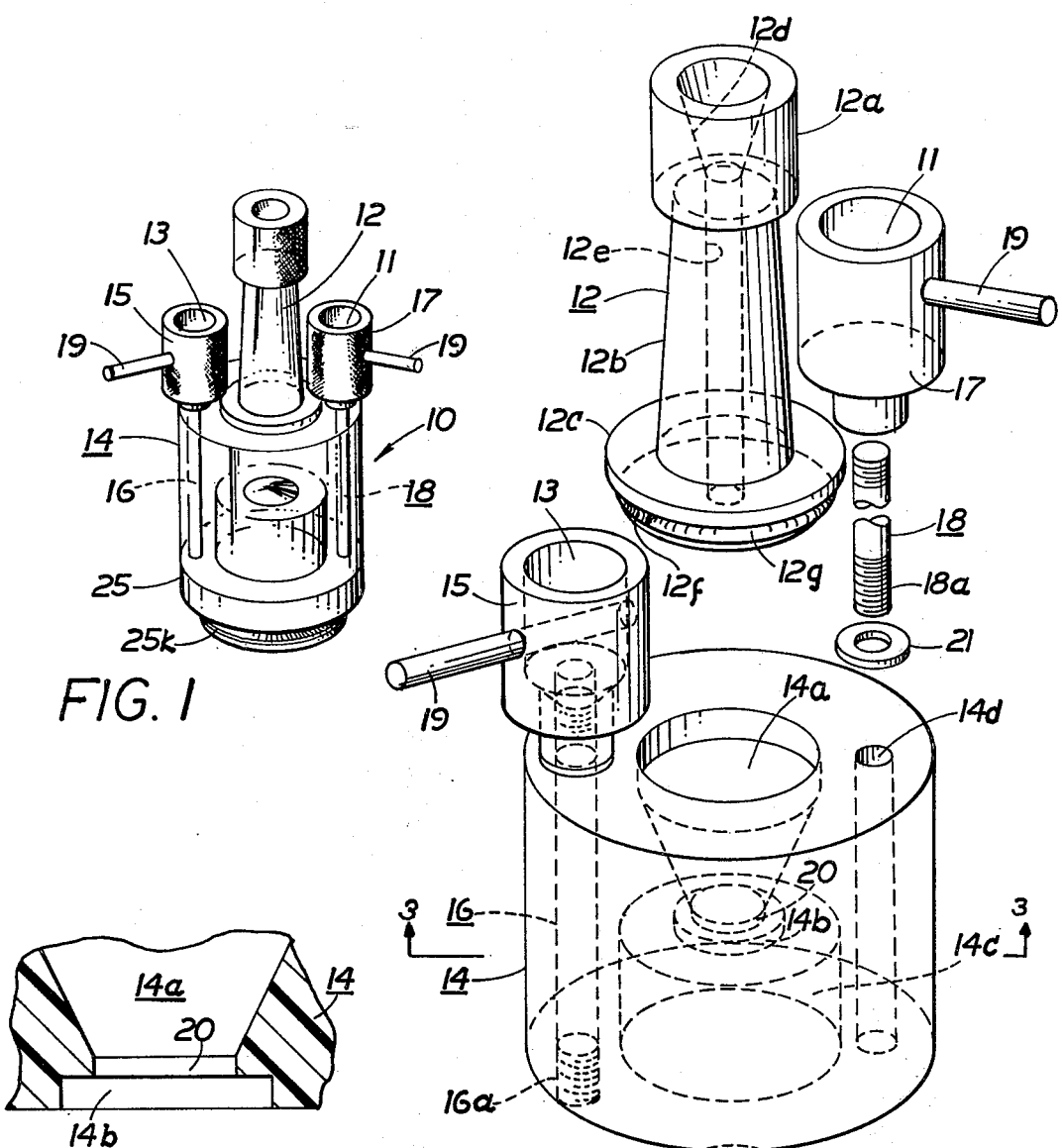
FIG. 1
FIG. 3
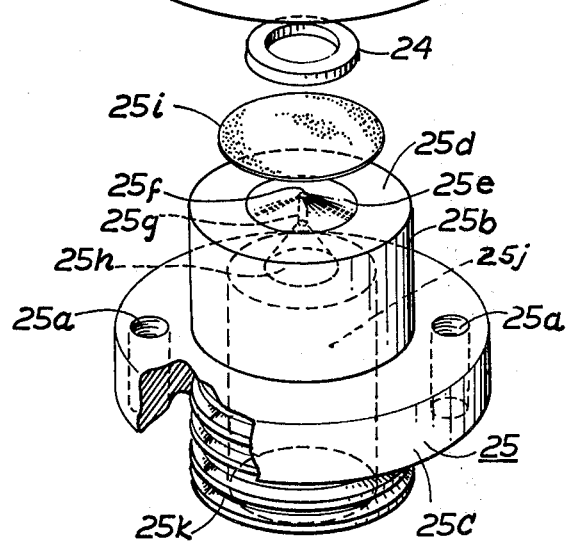
FIG. 2

ONCOTIC PRESSURE MEASUREMENT CELL

BACKGROUND OF THE INVENTION

1. Field of the Invention

This invention relates to instruments for measuring pressure and in particular to a cell for use in an instrument for measuring oncotic pressure of blood serum or plasma, or the like.

2. Prior Art

Instruments are known which have proved to be very useful diagnostic and measuring tools used for heart disease treatment, for example. They usually consist of an upper sample chamber into which a very small amount of the blood serum or plasma is placed and a lower chamber into which a reference solution is inserted. The lower reference chamber has an axial aperture and passageway which communicates with the upper sample chamber only through a semi-permeable membrane placed over the aperture. This membrane passes certain electrolytes and other constituents of the blood serum or plasma downward into the reference solution, but retains high molecular weight molecules such as proteins. Pressure exerted on the membrane by the passage of these constituents is sensed by a pressure transducer which is coupled to the lower end of the reference chamber. This pressure is quantified and displayed or recorded. Among other uses, the measurement of the oncotic pressure in heart disease helps to provide data indicating the risk of pulmonary edema and survival potential as well as aiding in prescribing the proper form of therapy.

One such prior art instrument is made almost entirely of plastic except for the pressure transducer coupled to the lower reference chamber. The upper sample chamber is threaded and is screwed onto the top of the reference chamber after the semi-permeable membrane disc has been placed between the chambers over the aperture in the reference chamber. While screwing the sample chamber onto the reference chamber exerted downward pressure upon a washer or ring placed above the disc, the screwing action often was sufficient to mutilate the disc. Thus, sometimes the operator would inadvertently destroy five or six discs before the semi-permeable membrane disc was held properly in place in an unmutilated state after the sample chamber was screwed on. Only if the disc is unmutilated can the disc effectively and perfectly form the right kind of barrier between the chambers. The necessity of having to produce this desired condition by repeated trials can result in delays which cannot be tolerated when the very life of the patient from whom the sample was drawn requires immediate and accurate diagnosis of his condition.

SUMMARY OF THE INVENTION

An oncotic pressure measurement cell which includes rigid elongated vertical members that are disposed upwardly from a lower reference chamber. These rigid members pass through passageways formed in the upper chamber which extend substantially the entire length of the upper sample chamber. Means which engage the upper ends of the rigid members are provided for regulating the downward pressure of the upper chamber without any rotational movement and for clamping the two chambers together once the deserved pressure is attained. In a preferred form the cell is made with a transparent plastic upper sample chamber and a metallic lower reference chamber.

BRIEF DESCRIPTION OF THE DRAWINGS

FIG. 1 is a perspective view of the novel cell according to the present invention;

FIG. 2 is an enlarged view, partly sectional, of the cell shown in FIG. 1 shown in an exploded view; and FIG. 3 is a sectional view of a part of the apparatus shown in FIG. 2 taken along the line 3—3 in FIG. 2.

DETAILED DESCRIPTION OF THE DRAWINGS

FIGS. 1 and 2 show a cell 10 having a transparent upper chamber 14 of generally cylindrical shape and made of a transparent plastic material. As shown, it is mounted upon a lower metallic chamber 25 whose lower end 25k is threaded for engagement with a correspondingly threaded portion of a pressure transducer such as a Statham Model P23DB. This transducer communicates via a passageway formed in the lower part of the lower chamber with the interior of the latter.

Formed in the generally cylindrical and transparent upper portion 14 are two passageways 14d through which two stainless steel rods 16 and 18 pass. Their respective lower ends 16a and 18a are threaded for screwing into the correspondingly internally threaded apertures 25a in the flanged portion of the lower chamber 25. Their upper ends which are similarly threaded pass through metal washers 21 and engage corresponding internally threaded threads of the cylindrically-shaped metallic thumb nuts 15 and 17 respectively. The outside surfaces of the nuts 15 and 17 are knurled. Bores 13 and 11 are provided along the axes of the nuts 15 and 17 which respectively communicate with the threaded lower portions of the nuts.

Each of the nuts 15 and 17 is also provided with transverse aligned apertures so that a pin 19 may be inserted therein (and then withdrawn) to enable the nuts 15 and 17 to be rotated more in a clockwise or counterclockwise direction than is possible by fingers alone. Movement in a clockwise direction causes the upper transparent chamber 14 to exert additional downward pressure upon the lower member 25.

A plastic closure or stopper member 12 which may be made of the same material as the transparent plastic sample chamber 14 is also provided. It has an axial passageway 12e starting with a flared opening 12d at the top and continuing untapered along the section 12b. This stopper is provided with a circular groove 12f around its lower portion into which a compressible O-ring 12g is inserted. After the sample is put into the upper chamber and before the pressure measurements are taken, the member 12 is moved downward so that its lower portion 12c is pressed into the upper edge of the opening 14a. The closure member 12 is also used to calibrate the cell. When first set up, it is desirable to test the cell so a suction line is attached to the opening 12d. A monometer is attached to the line and a vacuum of a desired magnitude is drawn as measured by the monometer.

As stated above, the lower ends 16a and 18a of the rods, which may be made of stainless steel, are screwed in and anchored in the correspondingly-threaded portions 25a of the stainless steel lower chamber 25. The latter comprises an upper cylindrically-shaped part 25b and an adjacent cylindrically-shaped portion 25c having a greater radius than 25b. Its lowermost portion is also generally cylindrical in shape and has about the same radius as the part 25b. This lowermost portion 25k is threaded to enable a pressure transducer to be screwed onto it as described earlier.

The upper surface 25d which may be made of stainless steel is polished to insure a good seal when the disc 25i is placed on it. It has a central portion 25e which inclines upwardly a slight amount. An aperture 25f is formed in the top of portion 25e along the axis of the member 25. The aperture communicates with a vertical passageway 25g which itself communicates with an angled opening 25h. This opening also communicates with the main cylindrical space 25j into which the reference fluid is initially placed. It will be noted that this fluid will communicate with an opening in the top of the pressure transducer which is screwed onto the lower portion 25k. The entire volume of the space below the aperture 25f is made to be smaller than in prior art oncotic pressure measuring devices. This feature, it is believed, helps the cell 10 to provide a faster output than has hitherto been obtainable by known similar devices.

There is also provided a semi-permeable plastic disc 25i which is placed on the generally horizontal upper surface 25d concentric with the aperture 25f. An annular washer 24 will, when the rods 16 and 18 are turned clockwise sufficiently, press down upon the semi-permeable disc 25i so that the disc's edges will be effectively sealed. The washer 24 fits into a corresponding space 14b provided in the chamber 14.

The chamber 14, which has been stated to be made of plastic, may be made of acrylic plastic, for example, all of whose surfaces have been polished so that there are no machining marks present.

Although in the embodiment shown in the drawings, the upper chamber is shown as being made of plastic, this is not an essential part of the invention. However, unlike metal, it allows the sample to be seen at all times, is quite resistant to corrosion and is easier to manufacture. The bottom chamber is preferably made of metal which makes for compactness, a solid base into which the vertical rods are enclosed and also for a stronger junction for the transducer (not shown) which is to be screwed onto portion 25k thereof. If the bottom chamber were made of plastic, it would have to be made heavier or larger to accommodate the great pressure exerted on it by tightening of the knurled nuts 15 and 17, especially when they are turned by the pin 19.

The washer 24 may be made of nylon rather than Teflon as used in other similar apparatus. Nylon, being more rigid than Teflon nonetheless enables the fluid-tight semi-permeable barrier to be maintained when it is pressed down by the chamber 14 against the semi-permeable disc 25i whose own compressibility and deformation characteristics impart a gasket property to it.

What is claimed is:

1. An oncotic pressure measurement apparatus comprising:
   (a) an upper chamber having a single opening toward the top thereof through which a sample to be analyzed may be passed into the interior of said chamber and an opening formed in the base thereof and also having a plurality of first passageways formed therein which extend substantially the entire length of said chamber,
   (b) a lower reference chamber having a second passageway formed therein toward the top thereof which communicates with the interior of said lower chamber,
   (c) a plurality of elongated rigid members whose lower ends are fixed to said reference chamber and which are adapted to pass through corresponding ones of said first passageways, and
   (d) means adapted to engage the upper ends of said rigid members when passed through said passageways for producing a predetermined downward pressure of said upper chamber without any appreciable rotary component of movement thereof.

2. The apparatus according to claim 1 wherein said upper chamber is formed from a light-transmitting plastic material.

3. The apparatus according to claim 1 wherein said lower chamber is formed from a metallic material.

4. The apparatus according to claim 1 wherein said elongated rigid members have upper ends which are threaded and wherein said means for producing a predetermined pressure comprise a plurality of manually operable, internally-threaded members adapted to be screwed on said upper ends into contact with said upper chamber thereby urging it into adjustable pressure against said lower chamber.

5. The apparatus according to claim 4 wherein said manually operable members have transverse apertures therein adapted to be engaged by lever means for increasing the pressure exerted by said upper chamber against said lower chamber beyond the pressure attainable solely by finger manipulation of said manually operable members.

6. The apparatus according to claim 4 wherein said manually operable members have knurled surfaces.

7. The apparatus according to claim 1 wherein said upper chamber has an interior space defined by downwardly-tapering walls and said lower chamber has an interior space partially defined by downwardly-tapering walls and partially defined by a cylindrical volume below said last-named tapering walls.

8. An oncotic pressure measurement apparatus comprising:
   (a) an upper sample chamber having an opening formed in the base thereof and also having a plurality of passageways formed therein which extend substantially the entire length of said chamber,
   (b) a lower reference chamber having an opening formed therein toward the top thereof, said upper chamber being fitted with a generally circular plastic means adapted to make contact with a deformable, semi-permeable barrier member placed over the said opening of said lower chamber, said contact being produced when said upper chamber is moved downwards against said lower chamber,
   (c) a plurality of elongated rigid members whose lower ends are fixed to said reference chamber and which are adapted to pass through corresponding ones of said passageways, and
   (d) means adapted to engage the upper ends of said rigid members when passed through said passageways for producing a predetermined downward pressure of said upper chamber without any appreciable rotary component of movement thereupon.

9. An oncotic pressure measurement apparatus comprising:
   (a) an upper sample chamber having an opening formed in the base thereof and also having a plurality of passageways formed therein which extend substantially the entire length of said chamber, said upper chamber being equipped with a single opening toward the top thereof through which a sample to be analyzed may be passed into the interior of said upper chamber and is further equipped with a normally releasable stopper dimensioned to fit frictionally within said single opening,
(b) a lower reference chamber having an opening formed therein toward the top thereof,
(c) a plurality of elongated rigid members whose lower ends are fixed to said reference chamber and which are adapted to pass through corresponding ones of said passageways, and
(d) means adapted to engage the upper ends of said rigid members when passed through said passageways for producing a predetermined downward pressure of said upper chamber without any appreciable rotary component of movement thereupon.

10. An oncotic pressure measurement apparatus comprising:
(a) an upper sample chamber having a generally frusto-conical enclosed space and an opening formed in the base thereof and also having a plurality of passageways formed therein which extend substantially the entire length of said chamber,
(b) a lower reference chamber having a generally frusto-conical upper portion disposed between and communicating with an opening formed therein toward the top thereof and a lower, generally cylindrical enclosed space,
(c) a plurality of elongated rigid members whose lower ends are fixed to said reference chamber and which are adapted to pass through corresponding ones of said passageways, and
(d) means adapted to engage the upper ends of said rigid members when passed through said passageways for producing a predetermined downward pressure of said upper chamber without any appreciable rotary component of movement thereof.

* * * * *